United States Patent [19]

Möller et al.

[11] 4,038,418

[45] July 26, 1977

[54] PROCESS OF SKIN TREATING WITH COMPOSITIONS CONTAINING POLYHYDROXYALKYLAMINES

[75] Inventors: Hinrich Möller, Dusseldorf-Benrath; Rainer Osberghaus, Dusseldorf-Urdenbach; Christian Gloxhuber, Haan; Siegfried Braig, Hildén, all of Germany

[73] Assignee: Henkel & Cie G.m.b.H, Dusseldorf-Holthausen, Germany

[21] Appl. No.: 572,270

[22] Filed: Apr. 28, 1975

[30] Foreign Application Priority Data

May 4, 1974  Germany .............................. 2421618

[51] Int. Cl.$^2$ ..................... A61K 7/00; A61K 31/13
[52] U.S. Cl. .................................. 424/358; 424/316; 424/325; 424/365
[58] Field of Search ............. 260/75 N; 424/316, 325, 424/358, 365

[56] References Cited

U.S. PATENT DOCUMENTS

| | | | |
|---|---|---|---|
| 3,748,309 | 2/1973 | Hunsucker | 260/75 N |
| 3,795,645 | 3/1974 | Hunsucker | 260/75 N |

OTHER PUBLICATIONS

Mellan, Industrial Solvents, Reinhold Pub. Co., N.Y., 2nd Ed., 1950, pp. 433–441.
Sagarin, Cos, Sci. & Tech., Intersci. Pub., N.Y., 1957, pp. 1163–1164.
Champion, Chem. Abs. vol. 75, 1971, Ab. No. 112800r.
Piette, Chem. Abs., vol. 70, 1969 Ab. No. 22851a.
Hamill, Chem. Abs. vol. 66, 1967, Ab. No. 1417k.

*Primary Examiner*—Albert T. Meyers
*Assistant Examiner*—Anna P. Fagelson
*Attorney, Agent, or Firm*—Hammond & Littell

[57] ABSTRACT

The present invention relates to compositions for the treatment of the skin containing from 1 to 20% by weight of a polyhydroxyalkylamine having the formula

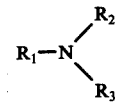

wherein $R_1$ is a member having 3 to 6 carbon atoms selected from the group consisting of dihydroxyalkyl and trihydroxyalkyl, and $R_2$ and $R_3$ are members selected from the group consisting of hydrogen, alkyl having from 1 to 4 carbon atoms, hydroxyalkyl having from 2 to 4 carbon atoms and dihydroxyalkyl having from 3 to 4 carbon atoms, and salts thereof, and the remainder up to 100% by weight inert cosmetic excipients; as well as the method of skin treatment.

6 Claims, No Drawings

PROCESS OF SKIN TREATING WITH COMPOSITIONS CONTAINING POLYHYDROXYALKYLAMINES

It is generally known that the protective measures for healthy skin include, among other things, maintaining a certain degree of hygroscopicity in the skin. If the substances, on which this degree of hygroscopicity and its constant restoration depend, are removed from the skin by environmental influences, such as repeated washing with substances which have a strong wetting and extracting effect, and the influence of chemicals and severe weather, alterations are produced in the horny layer of the skin which can greatly reduce its protective action against harmful environmental influences.

An object of the present invention is to provide a skin-care or skin-protection agent, which may maintain or increase the functional capacity of the skin in spite of harmful environmental influences, and which may effectively support the restoration of the horny layer, should any damage have been incurred.

Another object of the present invention is to obtain a cosmetic composition for the care and protection of the skin of warm-blooded animals consisting essentially of from 1% to 20% by weight of at least one polyhydroxyalkylamine selected from the group consisting of (1) compounds having the formula

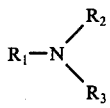

wherein $R_1$ is a member having from 3 to 6 carbon atoms selected from the group consisting of dihydroxyalkyl and trihydroxyalkyl, and $R_2$ and $R_3$ are members selected from the group consisting of hydrogen, alkyl having from 1 to 4 carbon atoms, hydroxyalkyl having from 2 to 4 carbon atoms and dihydroxyalkyl having from 3 to 4 carbon atoms, and (2) topically-inert acid salts thereof; and the remainder to 100% by weight of inert cosmetic excipients.

A yet further object of the present invention is the development of a process for the care and protection of the skin of warm-blooded animals comprising topically applying to the skin a thin but effective amount of the above composition.

These and other objects of the present invention will become more apparent as the description thereof proceeds.

The above objects have been achieved by the discovery of skin-care or skin-protection agents based on conventional constituents, such as emulsifiers, fatty substances, plant extracts, solvents, scents, thickeners and preservatives and containing from 1 to 20% by weight, preferably from 3 to 10% by weight, with respect to the total agent, of a di- and/or poly-hydroxyalkylamine or salt thereof having the general formula

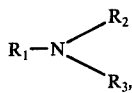

in which $R_1$ represents a di- or trihydroxyalkyl group having, from 2 to 6 carbon atoms, preferably from 3 to 6 carbon atoms, and $R_2$ and $R_3$ independent of one another represent hydrogen, an alkyl group having 1 to 4 carbon atoms, a hydroxyalkyl group having 1 to 4 carbon atoms, preferably 2 to 4 carbon atoms or a dihydroxylalkyl group having 2 to 4 carbon atoms, preferably 3 to 4 carbon atoms.

The compounds used in the compositions in accordance with the present invention are skin humectants which are extremely suitable for maintaining or restoring the water retention of the skin and thus for keeping the skin soft, supple and fully capable of performing its function.

In particular therefore, the invention relates to a cosmetic composition for the care and protection of the skin of warm-blooded animals consisting essentially of from 1 to 20% by weight of at least one polyhydroxyalkylamine selected from the group consisting of (1) compounds having the formula

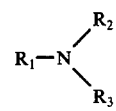

wherein $R_1$ is a member having from 3 to 6 carbon atoms selected from the group consisting of dihydroxyalkyl and trihydroxyalkyl, and $R_2$ and $R_3$ are members selected from the group consisting of hydrogen, alkyl having from 1 to 4 carbon atoms, hydroxyalkyl having from 2 to 4 carbon atoms and dihydroxyalkyl having from 3 to 4 carbon atoms, and (2) topically-inert acid salts thereof; and the remainder to 100% by weight of inert cosmetic excipients. In addition the invention relates to the process for the care and protection of the skin of warm-blooded animals comprising topically applying to the skin a thin but effective amount of the above cosmetic composition.

These polyhydroxyalkylamines can be produced according to generally known processes. For example, they can be produced (1) by reduction of the appropriate nitro compounds or (2) by alkoxylation of the appropriate amines. Thus 2-amino-2-methyl-propane-1,3-diol, 2-amino-2-ethyl-propane-1,3-diol, 2-amino-2-propyl-propane-1,3-diol, 2-amino-2-isopropyl-propane-1,3-diol can be obtained in accordance with the information given by Johnson and Degering in the Journal of Organic Chemistry, Vol. 8 (1943), pages 7 to 9, by catalytic reduction of the appropriate nitro compounds, the catalyst being Raney nickel. The following products; 1-amino-propanediol-2,3, 1-methylamino-propane-diol-2,3, 1-dimethylamino-propanediol-2,3, 1-ethylamino-propane-diol-2,3, 1-diethylamino-propanediol-2,3-are obtained in accordance with the information given by Knorr and Knorr in the Berichten der deutschen chemischen Gesellschaft (Reports of the German Chemical Society), Vol. 32 (1899), pages 750 to 757, by reacting glycidol with ammonia or the appropriate amines. In accordance with the information given by Schmidt and Witkendorf in the Berichten der deutschen chemischen Gesellschaft, Vol. 52 (1919), page 398, 2-amino-propanediol-1,3 can be obtained by catalytic reduction of 2-nitro-propanediol-1,3 in the presence of palladinized barium sulfate. The production of 2-amino-2-methyl-propanediol-1,3, 2-amino-2-ethyl-propanediol-1,3 and α,α,α-tris-(hydroxymethyl)-amino-methane by the reduction of appropriate nitro compounds by means of iron powder is described by Senkus in the Journal of Industrial and Engineering Chemistry Vol. 40 (1948), page 506ff. Further compounds to be used in accordance with the invention, such as N-(2,3-dihydroxypropyl)-isopropylamine, and N-(2,3-dihydroxypropyl)-dipropylamine are obtained in accordance with the information given by Malinovskii in the monograph "Epoxides and their Derivatives," Israel Program for Scientific Translations, Jerusalem 1965, page 234 ff by reacting appropriate amines with glycidol.

Examples of di- or polyhydroxyalkylamines to be used in accordance with the invention are 2-amino-propanediol-1,3,2-amino-2-methyl-propanediol-1,3, 2-amino-2-ethyl-propanediol-1,3, 2-amino-2-propyl-propanediol-1,3, 2-amino-2-isopropyl-propanediol-1,3, 1-amino-propanediol-2,3, 1-methylamino-propanediol-2,3,1-dimethylamino-propanediol-2,3, 1-ethylamino-propanediol-2,3, 1-diethylamino-propanediol-2,3, 1-propylamino-propanediol-2,3, 1-butylamino-propanediol-2,3 $\alpha,\alpha,\alpha$-tris-(hydroxymethyl)-amino-methane, N-(2,3-dihydroxypropyl)-isopropylamine, N,N-bis-(2,3-dihydroxypropyl)-methylamine, N-(2,3-dihydroxypropyl)-ethanolamine, N-(2,3-dihydroxypropyl)-diethanolamine, 2-($\beta$-hydroxy-propylamino)-2-methyl-propanediol-1,3, N-(2-ethyl-1,3-dihydroxy-2-propyl)-diethanolamine, 3-[$\alpha,\alpha,\alpha$-tris-(hydroxymethyl)-methylamino]-propanediol-1,2, N-($\alpha,\alpha,\alpha$-tris-[hydroxymethyl]-methyl)-diethanolamine. They are predominantly used in the form of their salts in the skin-care and skin-protection agents.

The acids employed for formation of the salts are those which are topically inert in the form of their salts. Preferably these acids are the mineral acids, lower alkanoic acids, hydroxycarboxylic acids and dicarboxylic acids. Example of the salts of the above-mentioned di- or polyhydroxyalkylamine are the halides, particularly chlorides, sulfates, phosphates, acetates, lactates, tartrates, citrates, glycolates, oxalates, fumarates, succinates and malates. The salts are preferably adjusted so that they have a pH value of 6 in a concentrated aqueous solution.

All the above-mentioned salts are colorless, odorless, completely stable products, having excellent physiological compatability, and do not have any disadvantageous effects on the skin-care and skin-protection agents with which they are mixed.

These salts have a high capacity to absorb water and an excellent water retention. Owing to these properties and their good physiological compatability they are highly suitable as skin humectants in cosmetic preparations, in particular in agents for the care and protection of the skin.

Skin-care and skin-protection agents to which special skin-care properties can be imparted by the addition of the di- and/or polyhydroxyalkylamines or their salts used in the present invention, are the conventional day creams, night creams and nourishing creams, baby creams, cleansing creams, cold creams, skin protection creams, glycerol creams, creams with special additives of animal or vegetable origin, sun protection or sun tanning creams, and sun protection emulsions, face lotions and after-shave lotions. The incorporation of the polyhydroxyalkylamines into the agents for care and protection of the skin may take place in the known manner by simple stirring-in or dissolving. In addition to the di- and/or polyhydroxyalkylamines or their salts, in accordance with the invention, the cosmetic preparations may contain the constituents normally present in them such as emulsifiers, fatty substances, plant extracts, preservatives, perfumes and solvents in the customary amounts. The pH value of the agents for the care and protection of the skin may be in the acid to neutral region (pH 5 – 7.0) and is appropriately adjusted to weakly acid values of about pH 6.

The following examples are intended to illustrate the subject of the invention without, however, limiting it to these examples.

EXAMPLES

The following compounds from among the di- and polyhydroxyalkylamines which are to be used in accordance with the invention as skin moisture-containing agents were subjected to the tests and used in recipes:

EXAMPLE A 3-amino-propanediol-1,2

In order to obtain the product, 10 gm of glycidol was mixed with 1000 gm of a 25% ammonia solution. After several hours the solution was concentrated by boiling and the oil which remained in the water after expulsion of the ammonia was fractionally distilled until decomposition was evident. For the tests the product which distilled at a temperature of 235° to 250° C and under a pressure of 320 mn, was used.

EXAMPLE B 2-ethyl-2-amino-propanediol-1,3

The product was obtained in the manner as described by Senkus in the Journal of Industrial and Engineering Chemistry (1948), page 506. A mixture of 280 gm of ferrous sulfate heptahydrate, 400 gm of iron powder, 500 ml of water and 10 gm of concentrated sulfuric acid was heated under reflux. A solution of 298 gm of 2-ethyl-2-nitro-propanediol-1,3 in 298 gm of water was slowly added to this mixture under energetic stirring. The stirring under reflux was continued for a further hour after the nitro alcohol had been added. Then, 100 gm of calcium hydroxide was added and the mixture was again stirred for a further hour. The solution was subsequently filtered and the residue was washed several times with water. 5 gm of barium hydroxide was added to the combined filtrates and the mixture was stirred for a further 15 minutes. The mixture was filtered, 5 gm of ammonium carbonate was added to the filtrate and, after energetic mixing, filtration was again effected. The water was subsequently distilled from the filtrate under atmospheric pressure and the residue was fractionated under reduced pressure. In this manner, 185 gm of 2-ethyl-2-amino-propanediol-1,3 was obtained.

EXAMPLE C $\alpha,\alpha,\alpha$-tris-(hydroxymethyl)-aminomethane

The product was obtained in accordance with the process of B above by the reduction of $\alpha,\alpha,\alpha$-tris-(hydroxymethyl)-nitromethane. The compound was used for the tests and in the recipes in the form of its hydrochloric acid salt.

EXAMPLE D 2-methyl-2-amino-propanediol-1,3

The product was obtained in the same manner as Example B by the reduction of 2-methyl-2-nitro-propanediol-1,3. In this case too the compound was used for the tests and in the recipes in the form of its hydrochloric acid salt.

EXAMPLE E

N-(2,3-dihydroxypropyl)-methylamine hydrochloride

The product was obtained in accordance with the information given by Malinovskii in the monography "Epoxides and their Derivatives," Israel Program for Scientific Translations, Jerusalem 1965, by reacting methylamine with glycidol.

EXAMPLE F

N,N-bis-(2,3-dihydroxypropyl)-methylamine hydrochloride

The product was obtained in ccordance with the information by Malinovskii by reacting 1 mol of methylamine with 2 mols of glycidol.

EXAMPLE G

N-(2,3-dihydroxypropyl)-diethanolamine hydrochloride

The product was obtained in accordance with the information by Malinovskii by reacting 1 mol of diethanolamine with 1 mol of glycidol.

The favorable behaviour of the compounds to be used in accordance with the invention with respect to water absorption capacity and water retention capacity was determined by means of test methods which are described in more detail hereinafter.

The determination of the water absorption capacity of the compounds in accordance with the invention took place by measuring the increase in weight during storage at 100% relative atmospheric moisture over a certain period of time, usually 48 hours. This was reported as mg water absorbed per 100 mg substance.

The water retention capacity was determined by measuring the residual water content of a moistened sample after storage at 0% relative moisture under a pressure of 12 mm Hg during a period of 45 minutes, 1½ hours and 8 hours. The moistening was made with 300 mg $H_2O$ per 100 mg substance. The residual water content was reported as mg of water per 100 mg of compound. The measured values listed in the following Table I were obtained.

TABLE I

Water retention capacity and water absorption capacity of di- and polyhydroxyalkylamines and their acid salts.

| product | water retention in mg/100 mg of substance | | | Water absorption in mg/ 100 mg after 48 hours |
|---|---|---|---|---|
| | after 45 mins. | after 90 mins | after 8 hrs. | |
| A | 18 | 11 | 3 | 237 |
| B | 33 | 22 | 7 | 153 |
| C-HCl | 93 | 58 | 31 | 368 |
| D-HCl | 80 | 76 | 6 | 464 |
| E-HCl | 74 | 35 | 9 | 211 |
| F-HCl | 126 | 75 | 14 | 354 |
| G-HCl | 112 | 83 | 17 | 405 |

In addition to the strong water absorption capacity, the considerable water retention capacity of the compounds to be used in accordance with the invention can be seen from the above table, and thus also their suitability as skin moisture-containing agents in skin-care and skin-protection agents.

The favorable action of the compounds, which are to be used in accordance with the invention with regard to capacity for the absorption and retention of water, was also determined by means of test methods which are described more fully hereinafter. A process for determining the equilibrium dampness, which constitutes a gauge for the water retention capacity, and the determination of the water retention, rehydration and elasticity of impregnated pig epidermis is described in these tests.

1. Determination of the equilibrium dampness

The substances (about 300 to 500 mg) to be tested were moistened with a defined quantity of water and exposed for 24 hours at 23° C to various relative atmospheric humidities (1%, 30%, 47%, 65%, 89% and 100% relative humidity). The amount of water absorbed or desorbed was determined gravimetrically and plotted on a graph. The relative humidity at which neither expulsion nor retention of water is effected, can be determined from the resultant curves. This value, which is designated as the equilibrium dampness, is a gauge for the water retention capacity of a substance. The lower the value, the more positive should be the assessment of the product.

The values are reported in Table II.

2. Tests on the pig epidermis a. To obtain the pig epidermis

As soon as the pigs have been killed, the bristles of the skin are cut off by means of a shearing machine (shearing head of 0.1 mm). The pigs are soaked for 3 to 5 minutes in warm water of 60° C, the epidermis is then peeled off and stored at −20° C until used.

b. Determination of the water retention and the rehydration of impregnated pig epidermis Stamped out pieces of epidermis (1 × 2 cm) were soaked for 2 hours in a 10% solution of the test substance, excess moisture was removed by means of a small press under standardized conditions and the pieces were dried for 24 hours, hanging free between 2 clamps in a 100 ml Erlenmeyer flask at 23° C both at 30% relative humidity and 50% relative humidity (set by sulfuric acid/water mixtures). The drying out of the impregnated test pieces to 10% of the initial weight was compared with the corresponding value of the epidermis which had been soaked only in water (blank value). In Table II, the improvement in the water retention and the rehydration as compared with the blank value is given in $\Delta\%$ of $H_2O$. The deviations in each double test amounted to a maximum of ± 2 absolute units. If greater deviations occurred, the test was repeated. The rehydration was determined analogously by drying the pig epidermis, which had been impregnated and from which the excess moisture had been removed, for 24 hours at 30% relative humidity, and by subsequent 24-hour incubation at 90% relative humidity.

c. Gauging of eleasticity of impregnated pig epidermis

Stamped out pieces of pig epidermis (1 × 6 cm) were soaked for 2 hours in a 10% aqueous solution of the substance which was to be tested, and excess moisture was removed from these pieces under standardized conditions. The test pieces were incubated for 24 hours, hanging free between 2 clamps both at 75% relative humidity and at 90% relative humidity and were stretched in a nipping tensile-testing machine (type: 1402) with 0 to 50 pound loading. The amount of stretch, which was measured in the Hooke range with loadings of 5 to 30 pound, was given in mm as a gauge for the elasticity.

The measured values obtained in the tests described above can be seen hereinafter in Table II.

TABLE II

Equilibrium dampness and measured values of pig epidermis

| product | Equilibrium dampness (% r.h.) | water retention in Δ% of H₂O after drying at 30% r.h. | water retention in Δ% of H₂O after drying at 50% r.h. | Rehydration Δ% water absorption at 90% r.h. | Stretch in mm with between 5 and 30 p loading at 90% r.h. | Stretch in mm with between 5 and 30 p loading at 75% r.h. |
|---|---|---|---|---|---|---|
| Blank value | — | 0 | 0 | 0 | 0.3 to 0.5 | 0 |
| A . HCl | 49 | 4 | 17 | 43 | 6.4 | 2.5 |
| A + Lactic acid (1:1) | — | 8 | 5 | 13 | — | — |
| B . HCl | 69 | 13 | 16 | 29 | 5.8 | 1.3 |
| B + Lactic acid (1:1) | — | 3 | 14 | 19 | — | — |
| D . HCl | 40 | 22 | 25 | 42 | 3.6 | 3.0 |
| D + Lactic acid (1:1) | — | 11 | 15 | 19 | 3.4 | 2.7 |

"—" = not measured

These afore-mentioned measured values of Table II, also confirm the suitability of the products which are to be used in accordance with the invention as skin moisture-containing agents in skin care and skin protection agents. The equilibrium dampness figures show that none of the products expel water until very low relative humidities have been reached.

In the following, a few examples of cosmetic preparations containing substances in accordance with the invention of skin humectants are given.

EXAMPLE 1

| Day cream, slightly greasy | Parts by Weight |
|---|---|
| Fatty acid partial glyceride Cutina MD® Dehydag | 6.0 |
| Stearic acid | 8.0 |
| Mixture of nonionic emulsifiers Eumulgin C 700® Dehydag | 3.0 |
| 2-octyl-dodecanol | 4.0 |
| Vegetable oil | 3.0 |
| Paraffin oil | 5.0 |
| Triethanolamine | 0.4 |
| 1,2-propylene glycol | 3.0 |
| Product A | 3.0 |
| Nipagin M® | 0.2 |
| Perfume oil | 1.0 |
| Water | 63.4 |

EXAMPLE 2

| Baby cream | Parts by Weight |
|---|---|
| Mixture of higher molecular esters, mainly mixed esters of pentaerythritol fatty acid ester and citric acid fatty alcohol ester Dehymuls E® Dehydag | 7.0 |
| Decyl oleate | 10.0 |
| Vaseline® | 10.0 |
| Wool fat | 5.0 |
| Boric acid | 0.2 |
| Talcum | 12.0 |
| Zinc oxide | 8.0 |
| Nipagin M® | 0.2 |
| Product B | 5.0 |
| Water | 42.6 |

EXAMPLE 3

| Night cream | Parts by Weight |
|---|---|
| Colloidally dispersed mixture of 90 parts of cetyl-stearyl alcohol and 10 parts of sodium lauryl sulfate | 10.0 |
| 2-Octyl-dodecanol | 12.0 |
| Vegetable oil | 7.0 |
| Wool fat | 2.0 |
| Glycerol | 1.0 |
| Product C | 5.0 |
| Nipagin M® | 0.2 |
| Perfume Oil | 1.0 |
| Water | 61.8 |

EXAMPLE 4

| Boro-glycerol cream | Parts by Weight |
|---|---|
| Colloidally dispersed mixture of 90 parts of cetyl/stearyl alcohol and 10 parts of sodium lauryl sulfate | 12.0 |
| 2-Octyl-dodecanol | 8.0 |
| Vegetable oil | 5.0 |
| Boric acid | 2.0 |
| Glycerol | 28.0 |
| Nipagin M® | 0.2 |
| Product D | 3.0 |
| Water | 41.8 |

EXAMPLE 5

| Sun protection cream | Parts by Weight |
|---|---|
| Mixture of higher molecular esters with fatty substances Dehymuls K® Dehydag | 30.0 |
| Decyl oleate | 15.0 |
| Light protection agent | 5.0 |
| Nipagin M® | 0.2 |
| Product C | 3.0 |
| Water | 46.8 |

EXAMPLE 6

| Face mask | Parts by weight |
|---|---|
| Mixtures of fatty acid partial glyceride with emulsifiers Cutina LE® Dehydag | 12.0 |
| Decyl oleate | 4.0 |
| Vitamin oil | 5.0 |
| Kaolin | 2.0 |
| Rice starch | 3.0 |
| Nipagin M® | 0.2 |
| Product D | 3.0 |
| Product A | 3.0 |
| Water | 67.8 |

EXAMPLE 7

| After-shave lotion | Parts by Weight |
|---|---|
| Oleyl/cetyl alcohol | 1.0 |
| Ethanol 96% | 67.5 |
| Menthol | 0.2 |
| Camphor | 0.2 |
| Peru balsam | 0.1 |
| Perfume | 0.5 |
| Hamamelis extract | 10.0 |
| Boric acid | 0.5 |
| Product C | 5.0 |
| Product B | 5.0 |
| Water | 10.0 |

EXAMPLE 8

| Face lotion | Parts by Weight |
|---|---|
| Cucumber essence | 15.0 |
| Citric acid | 0.2 |
| Ethanol 96% | 15.0 |
| Product D | 10.0 |
| Perfume | 1.0 |
| Water | 58.8 |

In place of the polyhydroxyalkylamine compounds in accordance with the invention mentioned in the above examples, others of the products may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

We claim:

1. A process for maintaining or restoring hygroscopicity in the skin for the protection of the skin of warm-blooded animals comprising topically applying to the skin a safe but effective amount as a moisturizing agent of a cosmetic composition consisting essentially of an aqueous medium adjusted to a pH between 5 and 7 containing from 1 to 20% by weight of at least one hydroxyalkylamine selected from the group consisting of (1) compounds having the formula

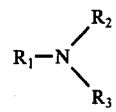

wherein $R_1$ is a member having from 3 to 6 carbon atoms selected from the group consisting of dihydroxyalkyl and trihydroxyalkyl, and $R_2$ and $R_3$ are members selected from the group consisting of hydrogen, alkyl having from 1 to 4 carbon atoms, hydroxyalkyl having from 2 to 4 carbon atoms and dihydroxyalkyl having from 3 to 4 carbon atoms, and (2) topically-inert acid salts thereof; and the remainder to 100% by weight of inert cosmetic excipients.

2. The process of claim 1 wherein the pH is 6.

3. The process of claim 1 wherein said at least one polyhydroxyalkylamine is present in an amount of from 3 to 10% by weight.

4. The process of claim 1 wherein said at least one polyhydroxyalkylamine is present as said topically-inert acid salt.

5. The process of claim 4 wherein said topically-inert acid salt is selected from the group consisting of the halide, the sulfate, the phosphate, the acetate, the lactate, the tartarate, the citrate, the glycolate, the oxalate, the fumarate, the succinate, and the malate.

6. The process of claim 4 wherein said topically-inert acid salt is the chloride.